(12) United States Patent
Elford

(10) Patent No.: US 6,924,308 B1
(45) Date of Patent: Aug. 2, 2005

(54) THERAPEUTIC PROCESS FOR INHIBITING NF-κB

(76) Inventor: Howard L. Elford, 3313 Gloucester Rd., Richmond, VA (US) 23227

( * ) Notice: Subject to any disclaimer, the term of this patent is extended or adjusted under 35 U.S.C. 154(b) by 661 days.

(21) Appl. No.: 09/123,620

(22) Filed: Jul. 28, 1998

Related U.S. Application Data

(60) Provisional application No. 60/054,230, filed on Jul. 30, 1997.

(51) Int. Cl.$^7$ .................. A61K 31/165; A61K 31/195; A61K 31/235
(52) U.S. Cl. .................. 514/533; 514/534; 514/575; 514/617
(58) Field of Search .................. 514/575, 533, 514/534, 617

(56) References Cited

U.S. PATENT DOCUMENTS

| | | | | |
|---|---|---|---|---|
| 4,252,322 A | * | 2/1981 | Orter .................. | 273/269 |
| 4,263,322 A | * | 4/1981 | van't Riet et al. .......... | 424/324 |
| 4,394,389 A | * | 7/1983 | van't Riet et al. .......... | 564/308 |
| 4,448,730 A | * | 5/1984 | van't Riet et al. .......... | 562/621 |
| 4,623,659 A | * | 11/1986 | van't Riet et al. .......... | 514/508 |
| 5,183,828 A | * | 2/1993 | van't Riet et al. .......... | 514/508 |
| 5,350,770 A | * | 9/1994 | Elford et al. .............. | 514/575 |
| 5,366,996 A | * | 11/1994 | Elford et al. .............. | 514/575 |

OTHER PUBLICATIONS

Casarett and Doull's Toxicology: The Basic Science of Poison, C.D. Klaassen, ed.; McGraw–Hill 1996, pp. 42.*
Salvemini et al 286 Science 304 (Oct. 1999).
Jenney et al 286 Science 906 (Oct. 1999).
Hogness & Johnson Qualitative Analysis and Chemical Equilibrium pp. 247–253, Henry Holt and Co., New York (1940).
Kharasch, Rowe and Urry J. Org. Chem 1951 pp. 905–913.
Meyer et al EMBO J. 12 2005 (1993).
Staal et al Methods Enzymol 252 168 ((1995).
M. Baringa "Life–Death Balance Within the Cell" Science 274, Nov. 1, 1996.
Roederer et al Proc. Nat. Acad. Sci. 87 4884 (Jun. 1990).
Barnes et al New England Journal of Medicine 336 1066 (1997).
Staal et al AIDS Research and Human Retroviruses 9 299 (1993).
Beg & Baltimore Science 274 782 (Nov. 1996).
Baruchel et al J. Leuko. Biol. 52 111 (Jul. 1992).
Hauser et al Can. Res. 50 3503 (Jun. 1990).
Green Science 274 1246 (Nov. 1997).
Kumar et al Science 278 1630 (Nov. 1997).
M. Baringa Science 280 32 (Apr. 1998).
Baeuerle et al Ann. Rev. Immun. 12 141 (1994).

* cited by examiner

Primary Examiner—James O. Wilson
Assistant Examiner—Leigh C. Maier
(74) Attorney, Agent, or Firm—Ladas & Perry LLP

(57) ABSTRACT

A therapeutic process is provided for the inhibition of NF-κB in mammals in whose cells NF-κB has been activated by an agency external to said cell.

11 Claims, No Drawings

THERAPEUTIC PROCESS FOR INHIBITING NF-κB

CROSS-REFERENCE

Provisional Application No. 60/054,230, filed Jul. 30, 1997

BACKGROUND OF THE APPLICATION

Eukaryotic cells contain a number of families of transcription factors which serve to rapidly induce expression of a variety of genes in response to extracellular stress or physiological signaling pathways. One important family of transcription factors mediating these responses is a factor named nuclear factor kappa B (NF-κB) and is composed of the NF-κB/Rel proteins. This factor, when in an active state, in turn activates genes involved in the mammalian body's response to inflammation, infection and stress. NF-κB is ubiquitously expressed but appears to play an important role in the etiology and progress of inflammatory disease, both chronic and acute, according to Barnes and Karin. NF-κB is rapidly activated by a wide variety of stimuli including cytokines, protein kinase C activators, viruses, ultraviolet radiation, immune stimuli and agents inducing oxidative stress leading to the production of reactive oxygen intermediates. It is believed that all of these act by means of specific protein kinases that degrade IκB whose biological role is to bind NF-κB and keep it in the inactive state in the cytoplasm. Antioxidants are also known to block the action of protein kinases indicating that reactive oxygen species may play an intermediary role. When IκB is phosphorylated, it is degraded by proteolytic reactions allowing the NF-κB to enter the nucleus and bind to DNA and transactivate target genes. The redox status of the cell appears to control the presence of IκB and therefore the activity of NF-κB. Antioxidants have been shown to inhibit the oxidative stress activation of NF-κB. Among the genes whose expression is increased by NF-κB are nitric oxide synthetase and cyclooxygenase-2, the latter being responsible for increased production of prostaglandins and thromboxane. NF-κB also regulates the expression of several genes that encode adhesion molecules which in turn recruit inflammatory cells.

Additionally, NF-κB plays a crucial role in the intracellular efficiency of gene expression and replication of the human immunodeficiency virus (HIV-1). Thus, inhibition of NF-κB could also play a role in the treatment of HIV-1 and other viral agents.

Finally, NF-κB status appears to play an important role in cancer treatment. For example, the discovery of Tumor Necrosis Factor (TNF) was hailed as a potential giant step in the treatment of cancer. It was found early on, however, that TNF did not kill most types of cancer cells. Apparently, TNF triggers one intracellular pathway that leads the cell to commit "suicide," in a process called apoptosis, and simultaneously triggers another that activates a key molecule that blocks this pathway. This second pathway involved genes that were turned on by NF-κB which protected the cancer cells from TNF killing. Recently four separate groups have uncovered information that supports this hypothesis. First, Baltimore and co-workers discovered that mice lacking NF-κB die before birth, apparently from massive die-off of liver cells. This finding implied that NF-κB protects embryonic liver cells from committing suicide. Next, Sonenschein's group found that inhibiting NF-κB causes the B-cells of the immune system to die of apoptosis. These results were followed up by papers from the Baltimore group, from Verma's group at the Salk Institute and from Baldwin's group at University of North Carolina. Baltimore's group compared the effect of TNF on cells from treated mice lacking NF-κB and cells from normal mice. The cells from the normal mice survived but the cells from the mice lacking NF-κB died. Both other groups treated a variety of cells (tumor and non-tumor) with a mutant form a Ikb that acts to keep NF-κB irreversibly shackled in the cells cytoplasm. Cells treated with Ikb were all killed by TNF. It has been found that other oncolytic agents act on tumor cells in the same way as TNF; i.e., radiation and danorubicin. Therefore, the inhibition of NF-κB may enhance the anticancer activity of a number of chemotherapeutic agents that cause cell damage leading to cell suicide via the apoptotic process. Therefore we are providing a superior therapeutic process for NF-κB inhibition.

OBJECTS OF THE INVENTION

It is an object of the invention to provide a therapeutic process from the description which follows.

DESCRIPTION OF THE INVENTION

In fulfillment of the above and other objects, this invention provides a therapeutic process of the inhibition of NF-κB in mammals in whose cells NF-κB has been activated which comprises administering to a mammal in whose cells NF-κB has been activated and in need of treatment, an NF-κB inhibitory amount of a free-radical scavenging drug of the following formula:

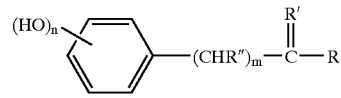

wherein n is 2–5, m is 0 or 1, R is $NH_2$, NHOH, $OC_{1-3}$ alkyl or 0-phenyl, R' is 0, NH or NOH and R" is H or OH. Also included are the pharmaceutically acceptable salts of compounds according to the above formula where chemically feasible. Also included within the scope of this invention are the phenolic acetyl derivatives of compounds according to the above formula. Such acetyl derivatives act as "prodrugs" in that they are converted by the mammalian body to the corresponding compound having entirely unesterified phenolic hydroxyls, which are the therapeutically active drugs.

Illustrative of the polyhydroxy-substituted phenyl ring in the above formula are included 2,3-dihydroxyphenyl, 3,4-dihydroxyphenyl, 2,5-dihydroxyphenyl, 2,6-dihydroxyphenyl, 2,3,4-trihydroxyphenyl, 2,3,5-trihydroxyphenyl, 3,4,5-trihydroxyphenyl, 2,4,5-trihydroxyphenyl, 2,3,4,5-tetrahydroxyphenyl, pentahydroxyphenyl and the like groups.

In the above formula, when m is 1 and R" is H, a phenylacetic acid derivative is denominated. When m is 1 and R" is OH, a mandelic acid derivative is represented. When m is 0, R is NHOH and R' is O, N-hydroxybenzamide (formerly, a benzohydroxamic acid) is represented; when R is $NH_2$ and R' is NH, a benzimidamide (formerly a benzamidine) is represented; when R is NHOH and R' is NH, an N-hydroxy benzimidamide (formerly a benzamidoxime) is shown; when R is NHOH and R' is NOH, and N,N'-dihydroxy benzimidamide (formerly an hydroxyamidoxime) is represented; and when R is 0-alkyl or 0-phenyl and R' is NH, the resulting compounds are benzimidates (rather than benzamidates as previously). In the above formula, when R is $OC_{1-3}$ alkyl, the alkyl groups represented include methyl, ethyl, isopropyl and n-propyl.

Compounds represented by the above formula are fully illustrated in U.S. Pat. No. 4,263,322, 4,623,659, references cited therein. In particular, the compounds listed in Cols. 2 and 3 of U.S. Pat. No. 4,623,659 illustrate the scope of the compounds represented by the above formula (always remembering that the approved nomenclature for these structures has changed since 1983 when the application which resulted in that patent was filed) and the disclosure of U.S. Pat. No. 4,623,659 is incorporated herein, and made a part of, by reference.

It will be apparent to those skilled in the art that other free radical scavengers in addition to those enumerated above would also be operative in the processes of this invention and are therefore included within its scope.

Three extremely active NF-κB inhibitors represented by the above formula are Didox (N,3,4-trihydroxybenzamide); Trimidox (N,3,4,5-tetrahydroxybenzamide) and Amidox (N,3,4-trihydroxybenzimidamide).

Compounds represented by the above formula may be administered in saline to mammals in whom NF-κB has been triggered by inflammation, a viral disease, radiation or an anticancer drug, via the intraperitoneal, intravenous, intramuscular, intradermal or intrathecal routes in accordance with the skill of the art. Similarly, it is well within the skill of the art when coupled with published dosages in connection with other diseases in which treatment with a free-radical scavenger might be beneficial to prepare oral medications containing Didox, Amidox, or Trimidox as the above drug, i.e., tablets, filled gelatin capsules, or liquid formulations. As will be apparent also to those skilled in the art, the effective dose levels will vary according to the mode of administration. For example, oral dose levels would be higher, and intravenous or intramuscular levels lower in general than intraperitoneal dose levels. Drug carriers may also be employed and the NF-κB inhibiting agents of this invention can be combined in a combination dosage forms with, or be administered at the same time as, other inhibitory agents. Phenol-acetylated compounds according to the above formula, although called "pro-drugs" herein, can also be considered as a special type of drug carrier.

I claim:

1. A process for inhibiting NF-κB in a mammalian cell in which NF-κB has been activated by an agency external to said cell which comprises administering to the mammal in whose cells NF-κB has been activated on NF-κB inhibiting amount of a drug represented by the formula:

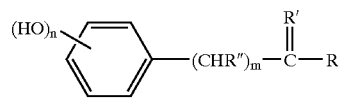

wherein n is 2–5, m is 0 or 1, R is $NH_2$, NHOH, $OC_{1-3}$ alkyl, or 0-phenyl, R' is 0, NH or NOH and R" is H or OH, or a pharmaceutically-acceptable acid addition salt or acylated phenol derivative thereof.

2. A process according to claim 1 in which the external agency activating NF-κB in an inflammatory process includes, but is not limited to, a cytokine, an activator of protein kinase B, a virus or an oxidant.

3. A process according to claim 1 in which the external agency activating NF-κB is a drug or radiation administered to the host mammal in a chemotherapeutic process used in the treatment of cancer.

4. A process according to claim 1 in which the administered NF-κB inhibitor is a free-radical scavenger.

5. A therapeutic process according to claim 1 in which the NF-κB inhibitor is N,3,4-trihydroxybenzamide.

6. A therapeutic process according to claim 1 in which the NF-κB inhibitor is N,3,4,5-terahydroxybenzamide.

7. A therapeutic process according to claim 1 in which the NF-κB inhibitor is N,3,4-tetrahydroxybenzimideamide.

8. A therapeutic process according to claim 1 in which the NF-κB inhibitor is a ribonucleotide reductase inhibitor.

9. A process according to claim 1 in which the external agency activating NF-κB is the reslt of a tissue transplant, an organ transplant or a cell transplant in a mammal.

10. A process according to claim 1 in which the external agency activating NF-κB is arteriosclerosis.

11. A process according to claim 1 in which the external agency activating NF-κB is diabetes.

* * * * *